United States Patent [19]

Chang et al.

[11] Patent Number: 5,141,744

[45] Date of Patent: Aug. 25, 1992

[54] INSECTICIDE DELIVERY SYSTEM AND ATTRACTANT

[75] Inventors: Frank N. Chang, Dresher; Michael J. Gehret, Lebanon, all of Pa.

[73] Assignee: Temple University, Philadelphia, Pa.

[21] Appl. No.: 389,598

[22] Filed: Aug. 3, 1989

[51] Int. Cl.⁵ .................. A01N 25/10; A01N 63/00; A01N 63/04; C12N 11/08

[52] U.S. Cl. .................. 424/93; 424/84; 424/409; 424/485; 424/486; 424/487; 424/488; 424/93 C; 424/93 D; 424/93 L; 424/93 Q; 424/93 T; 435/178; 435/180

[58] Field of Search .......... 424/78, 81, 484, 485, 424/486, 488, 84, 93, 405, 409, 487; 514/53, 54, 944; 426/1, 2; 119/1; 43/55; 435/178, 182, 101, 180

[56] References Cited

U.S. PATENT DOCUMENTS

| | | | |
|---|---|---|---|
| 3,070,495 | 12/1962 | Esenther et al. | 424/2 |
| 3,337,395 | 8/1967 | Page | 424/93 |
| 3,541,203 | 11/1970 | Fogle | 424/464 |
| 3,767,790 | 2/1972 | Guttag et al. | 424/81 |
| 4,178,366 | 12/1979 | Bedding | 424/93 |
| 4,304,906 | 12/1981 | Kang et al. | 435/101 |
| 4,311,795 | 1/1982 | Kang et al. | 435/101 |
| 4,326,052 | 4/1982 | Kang et al. | 536/123 |
| 4,326,053 | 4/1982 | Kang et al. | 536/123 |
| 4,363,798 | 12/1982 | D'Orazio | 424/84 |
| 4,369,176 | 1/1983 | Ott | 424/84 |
| 4,377,636 | 3/1983 | Kang et al. | 435/101 |
| 4,385,123 | 5/1983 | Kang et al. | 435/101 |
| 4,394,447 | 6/1983 | Cadmus et al. | 435/101 |
| 4,434,231 | 2/1984 | Jung | 435/180 |
| 4,450,233 | 5/1984 | Mimura et al. | 435/182 |
| 4,615,883 | 10/1986 | Nelsen et al. | 424/84 |
| 4,670,250 | 6/1987 | Baker | 424/419 |
| 4,695,455 | 9/1987 | Barnes et al. | 435/69.1 |
| 4,701,326 | 10/1987 | Nelsen et al. | 424/84 |
| 4,707,355 | 11/1987 | Wilson | 424/84 |
| 4,732,762 | 3/1988 | Sjogren | 424/409 |
| 4,743,247 | 5/1988 | Wong | 424/468 |
| 4,753,799 | 6/1988 | Nelson et al. | 424/408 |
| 4,859,377 | 8/1989 | Shasha et al. | 424/410 |

FOREIGN PATENT DOCUMENTS

250908  1/1988  European Pat. Off. .............. 424/93

OTHER PUBLICATIONS

"Starch encap. Bacillus", Dunkle et al, Environ Entomol 17 1:120 (1985).
"Encap. of Nematodes with Calcium Alginate", Environ. Entomol. 14:572-574 (1985) Kaya et al.
"Encap. of Mosquito fungal pathogen in Calcium Alginate" JAMCA 33:450-59 (1987); Axtell et al.
Gel-Gro, ICN Biochemicals-Div. of ICN Biomedicals, Inc.

*Primary Examiner*—Jeffrey E. Russel
*Attorney, Agent, or Firm*—Ratner & Prestia

[57] ABSTRACT

An insecticidal composition in the form of a hydrated macrogel containing at least one species of entomopathogen and a hydrated water retentive compound which acts as a water-reservoir for the entomopathogen. Optionally, the macrogel contains attractants, in particular raffinose and gamma-irradiated, fungal-decayed wood.

28 Claims, No Drawings

INSECTICIDE DELIVERY SYSTEM AND ATTRACTANT

BACKGROUND OF THE INVENTION (1) Field of the Invention

This invention relates generally to insecticidal delivery systems, in particular to systems for the delivery of natural entomopathogens to insect-infested loci.

(2) Description of Related Art

Use of natural biological predators to control populations of harmful insects has attracted increasing interest as the shortcomings of chemical pesticides have become more obvious. Despite the uncontroverted success of DDT in practically eliminating malaria as a worldwide scourge and the stunning increases in agricultural productivity associated with the judicious application of pesticides, attention has been increasingly focused on the negative effects of chemical agents.

Living insecticidal agents, delivered under controlled conditions, have narrow host ranges and can control the spread of specific hosts, without affecting natural predators or beneficial organisms. Such agents, herein termed entomopathogens, include bacteria, such as *Bacillus thuringiensis*, baculoviruses, fungal pathogens, and insect nematodes. These biological insecticides are generally more costly and less persistent than their chemical counterparts. Many entomopathogens are susceptible to rapid environmental degradation caused by exposure to ultraviolet radiation, heat, desiccation, substrate pH, or microbial competition, severely limiting their practical use. Consequently, efforts have been directed to both reducing manufacturing costs and maintaining the conditions necessary for preserving the activity of bioinsecticides to increase their competitiveness versus chemical insecticides.

Encapsulation technology similar to that developed for chemical insecticides has been used to protect and preserve entomopathogens. For example, microencapsulation of nuclear polyhedrosis viruses with polyvinyl alcohol, ethylcellulose, and other polymers has been reported. The microencapsulation of insecticidal crystal spore complexes of Bacillus thuringiensis has also been reported in the form of granules of approximately 500 microns diameter. Polysaccharides such as starch and cellulose have also been crosslinked with borate, calcium or xanthide to produce matrices that can be processed into granules of desirable sizes, densities and porosities. Unfortunately, this encapsulation process is not suited for entomopathogens because the presence of hydrogen peroxide, borate and alkaline pH in the crosslinking process kills the living insecticide.

Insect nematodes (Steinernematidae, Heterorhabditidae, Mermithidae) have been shown to be highly effective bioinsecticides (Poinar, "Nematodes for Biological Control of Insects", CRC Press, Inc., Boca Ratan, Fla., 1979). However, insect nematodes require moist conditions to survive and function. When nematodes are dried they lose activity rapidly; subsequent rehydration fails to restore the lost activity. One method of preserving nematodes in a moist environment is via the microencapsulation processes of U.S. Pat. Nos. 4,615,883, 4,701,326, and 4,753,799. This art microencapsulates the nematodes in calcium alginate. The alginate microcapsules, however, have several drawbacks. They are fairly large and rigid and consequently are not appealing to insects as well as being out of the chewing range of smaller insects. Additionally, the ability of the alginate microcapsules to maintain moisture conditions conducive to survival of the nematodes has also been questioned (Dunkle and Shasha, Environ. Entomol., Vol. 17, 120–126, 1988). To reduce the rate of desiccation, others have used water thickeners, mineral oil, or surfactants. See, for example, U.S. Pat. No. 4,178,366. With insect nematodes most of these approaches are ineffective in preserving the moisture content and consequently the biological activity. Some have adverse effects on biological activity or repel the target insects, thereby making them ineffective for their intended purpose.

There exists a need therefore for a low cost, reliable method of protecting entomopathogens from desiccation without interfering with their ability to infect and destroy undesirable insects.

SUMMARY OF THE INVENTION

This invention provides a novel composition and method for maintaining the viability of entomopathogens while providing a convenient means of delivering the entomopathogens to sites of insect infestation. These goals are accomplished by the provision of an insecticidal composition in the form of a hydrated macrogel. The macrogel contains at least one species of entomopathogen and a hydrated, water retentive polymer which serves as a reservoir of moisture for the entomopathogen. The macrogel itself is a continuous insect-consumable matrix, preferably made from a polysaccharide. The entomopathogen and the water reservoir are independently dispersed throughout the matrix. Also optionally dispersed in or on the matrix are attractants, food, feeding stimulants, complementary pesticides, and UV protectants.

A preferred attractant for termites is irradiated, preferably gamma-irradiated, fungal-decayed wood which is optionally dispersed in or on the macrogel, in proximity thereto, or may be used independently to attract termites to the gel or to other termiticidal compositions.

DETAILED DESCRIPTION OF THE INVENTION

The problem of desiccation of entomopathogens such as insect nematodes, bacteria, baculoviruses, or fungal pathogens can be substantially ameliorated by the hydromacroencapsulation of this invention. As used herein the term "hydromacroencapsulation" refers to distributing entomopathogens, particularly nematodes, in a continuous insect-consumable matrix, along with a source of water for the entomopathogens. The final product is thus a continuous gel in which the nematodes or the like are embedded, together with a source of moisture, and, optionally, other additives, such as insect attractants, insect feeding stimulants, and such stabilizers as may be required by the contemplated use of the insecticidal macrogel.

By the process of this invention, the entomopathogens are suspended in an aqueous solution of a gel-forming matrix in the presence of an inert water retaining polymer. Gelation is then induced by whatever means are appropriate for the selected matrix. The resultant insecticidal macrogel then contains a distribution of entomopathogens and water reservoirs. The macrogel may be stored for an indefinite period without adverse effects on the viability of the entomopathogens and may be cut into smaller pieces as desired. The macrogel may also take the shape of a cylinder, cone, sphere, cube, rectilinear solid, funnel, tube or spike.

In one embodiment of this invention a solution of nematodes, water retentive polymer, and gel precursor is sprayed on the site where control is desired. Gelation is then induced by spraying with a solution of cations, forming a thin film of insecticidal macrogel directly on the designated locus.

The gel-forming matrix is selected from natural, naturally derived, and synthetic polymers, with the provisos that the matrix per se and the gelation conditions are neither harmful to the entomopathogens nor interfere with the effectiveness of the pathogens. Suitable gel-forming matrices include, but are not limited to, agarose, carbopols, carrageenan, dextran, guar gum, and other heteropolysaccharides, such as gellan gum. One advantage associated with the use of the natural polysaccharides is that these are often attractive as food for the insects whose demise is desired.

A preferred matrix is the cationically gellable heteropolysaccharides, such as those disclosed in U.S. Pat. No. 4,326,052 and U.S. Pat. No. 4,326,053, the disclosures of which are incorporated by reference herein. A suitable variety of this material is available commercially as Gel-Gro ® gellan gum from ICN Biochemicals, Cleveland, Ohio.

An important aspect of the hydromacroencapsulation process of this invention is the selection of a gel-forming material which is a liquid at room temperature or at temperatures which are not detrimental to the entomopathogens and which can be induced to gel at a predetermined time by either mixing or spraying with a gelling agent. Such controlled gelation is important during manufacturing of the gels to avoid premature gelation and clogging of equipment. During the production of macrogels in discrete containers, a gelling time of 2 to 15 minutes is preferred. For spraying applications, instantaneous gelation is preferred to avoid runoff or dripping.

The gelation time of the Gel-Gro ® gellan gum used in the Examples which follow is easily controlled by varying the polymer concentration, the concentration and type of gelling agent, and the temperature. Preferably, the Gel-Gro liquid polymer concentration is between 0.4% and 5.0% by weight, the gelling agent is a cation, and the concentration of gelling agent is from 0.1 mM to 500 mM. Most preferably, the polymer concentration is from about 0.6% to 1.2% by weight, the gelling agent is a divalent cation, and the cation concentration is from about 0.5 mM to 25.0 mM. The most preferable conditions result in gelation times of about 1 to 15 minutes. When spraying formulations are desired, a cation concentration in excess of 25 mM is preferred to obtain rapid gelation.

Suitable divalent cations include barium, calcium, copper(II), iron(II), magnesium, manganese, and zinc(II). Monovalent cations such as ammonium, cesium, lithium, potassium, and sodium, may also be used to induce gelation, albeit at higher concentrations. Trivalent ions such as aluminum and iron(III) are also useful.

The hydrated, water retentive compound which is incorporated into the gel as the water reservoir for the entomopathogen is typically a water-absorbing polymer, such as a hydrophilic acrylic, acrylamide, or polyurethane polymer. Such polymers, commonly known as hydrogels, will absorb and retain several hundred times their weight in water and will slowly release the absorbed water. Representative examples of these materials are California Crystals ®, a water-absorbing acrylic polymer available from J & G Agrow-tek, Rancho Cordova, Calif. and Water Grabber ®, a water-absorbing acrylamide from FP Products, Inc., Atlanta, Ga. Other materials which exhibit similar affinities for water may be substituted. The amount of hydrated, water retentive polymer present in the matrix is generally about 25% to about 75%, although the choice and concentration of pathogen and the envisioned environment may lead to significant departures from these norms. Optionally, a heteropolysaccharide, such as Gel-Gro ® gellan gum, may be used without water retentive polymer, if the intended use permits of this approach.

As previously noted, the entomopathogen is selected from among those pathogens which control noxious insect infestations. Baculoviruses, such as nuclear polyhedrosis virus, bacteria, such as *Bacillus thuringiensis*, fungal pathogens, such as *Beauveria bassiana*, *Metarrhizium anisopliae*, and *Nomurea releyi*, and nematodes, such as *Neoplectana carpocapsae* and Heterorhadiitis heliothidis are among the more useful pathogens. Selection of the entomopathogens is not limited to those described herein, but is well within the purview of one skilled in the art of natural predation. Nematodes are particularly well-suited for the practice of this invention. However, the only limitations o the pathogens are that they not be inactivated by the conditions of gelation or the composition of the macrogel. Since the entomopathogens will reproduce in the insect host, only a few need be incorporated in a discrete sample of gel to provide control. Of course, millions of pathogens may be easily incorporated. In the practice of this invention, we have found that nematode concentrations of up to about 500,000 per milliliter are most useful. For other pathogens, such as bacteria, the gel may contain as much as 20% by weight.

A further aspect of the current invention is the optional use of agents capable of attracting insects to the gels and stimulating the insects to feed on the gels. Such agents, also termed baits, can include, for example, foods used in the commmercial rearing of insects, pheromones, chemical attractants, and the like. Art-recognized insect attractants include sucrose, wheat germ, and bran. In the course of this development, it has been discovered that raffinose is a highly effective feeding stimulant for certain insects.

In one aspect of this invention a new attractant for termites is provided. U.S. Pat. No. 3,070,495, incorporated by reference herein, disclosed the peculiar efficacy of fungal-decayed wood for attracting termites. This patent reported that termite-attracting principle could be obtained by the fungal-induced decay of coniferous and deciduous woods. Brown rot, white rot, and soft rot were all effective in generating the attractant. Extracts of the decayed wood were also attractive to termites. The use of the fungal-decayed wood, however, presents an environmental problem in that live wood-decaying fungi are released. Although the fungi may be killed by autoclaving the fungal-decayed wood, the high temperatures involved also inactivate the termite-attracting principle. This problem has been resolved by our discovery that gamma irradiation of the fungal-decayed wood kills the fungi, and not only preserves, but actually enhances the ability of the decayed wood to attract termites.

The insecticidal macrogel of this invention may include other additives, such as UV protectants. In one embodiment of this invention, a protectant and/or attractant composition is coated or merely distributed on the exposed surface of the macrogel, thereby providing the desired functionality without the need to incorporate the additive into the macrogel itself. This is particularly attractive for additives which may be toxic to the embedded entomopathogen. Optionally, the macrogel may be supplied in colored containers, thus reducing the susceptibility to degradation by sunlight.

It is intended that the macrogel be used in the form which is most efficacious for the insect control situation involved. To this end, macrogel may be formed in discrete containers for transfer directly to the sites of control, may be prepared in large blocks which can be shaved or trimmed to provide the desired dosage, and even may be formed right at the site of infestation.

Among the many advantages of this invention are:

1. More than one entomopathogen may be included in the macrogel thereby providing a diverse insecticidal spectrum.
2. Attractants, feeding stimulants, stabilizers, protectants, and chemical insecticides may be employed in the matrix, as surface agents, or both, depending upon their compatibility with the gel and the entomopathogen, and the needs of the situation.
3. The macrogels are simple to manufacture and highly efficient in incorporation of all ingredients.
4. The soft, hydrated macrogels are easily consumed by all kinds of insects ranging from small ants to giant caterpillars.

The following examples are presented to illustrate the basic features of the invention but are not intended to, and should not be construed as, placing any undue limitations on the invention as claimed.

EXAMPLE 1

A solution of purified gellan gum (Gel-Gro® gellan gum) was prepared by dissolving 0.2g of the gum in 10 mL of hot deionized, distilled water to make a 2% solution. This solution was cooled to room temperature.

A stock of fully swelled and expanded water retentive polymer was prepared by soaking small crystals of a water-swellable acrylic polymer (California Crystals)® in water for about one day. The swollen crystal gels were then pushed through a wire screen to produce pieces that were approximately 1 mm in length, width, and height. Enough water swollen pieces were added to a 1 mL aqueous dispersion containing approximately 10,000 nematodes (*Neoaplectane carpocapsae*) to increase the volume to 2 mL.

To this nematode dispersion, 2 mL of the 2 wt % gellan gum solution was added with gentle mixing. 0.2 mL of 20 mM calcium chloride was then added and the resultant mixture quickly poured into plastic tubes. Gelation was complete in about ten minutes and the tubes were then capped.

When capped, the insecticidal nematode macrogels are stable for at least one year when stored at 16° C. or lower. At room temperature, the macrogels retain biological activity for at least six months.

When nematode-containing macrogels without water retentive polymers were uncapped and exposed at room temperature, the macrogels dehydrated rapidly, and after one week, the gels were totally dry and few live nematodes were present. In contrast, uncapped nematode-containing macrogels with water retentive polymer were still moist after one week at room temperature and at least 95% of the nematodes were still alive.

EXAMPLE 2

A 2% gellan gum solution was prepared as in Example 1. To this solution was added with vortexing an equal volume of the nematode-water retentive polymer dispersion of Example 1, also containing 2 mM calcium chloride. The resulting macrogel was then capped and stored below 16° C.

EXAMPLE 3

A nematode-containing macrogel was prepared following the procedure of Example 2 in plastic test tube caps (1 cm diameter, 1.8 cm height). Raffinose (2% by weight) was also present in the nematode-water retentive polymer dispersion. Two of these macrogel samples were placed in a large tray (40×20 cm, 15 cm high), layered with wood shavings and having both water and gourmet insect diet present. Ten German cockroaches (*Blatella germanica*) were introduced into the tray. After 3 days, all the cockroaches were dead. When dissected 4 days later, each contained 10 or more live nematodes within the body. Nematode-free macrogel placed in a control tray had no effect on cockroaches.

EXAMPLE 4

Nematode-containing macrogels prepared as in Example 3 were tested for efficacy against a representative cross-section of insect pests. The tests were conducted in 250 mL beakers containing both insect food and a source of water. The results are summarized below.

| INSECT | TIME TO KILL | NEMATODES IN BODY CAVITY 10 DAYS LATER |
|---|---|---|
| Southern armyworm (*Spodoptera eridania*) | <2 days | 1000 |
| Mexican Bean Beetle (*Epilachna varivestis*) | <2 days | 500 |
| Black cutworm (*Agrotis ipsilon*) | 1-2 days | 1000 |
| Boll weevil (*Anthonomus grandis*) | <2 days | Not Counted |
| Tobacco budworm (*Heliothis virescens*) | <3 days | Not Counted |
| Corn rootworm (*Diabrotica spp.*) | 1-2 days | 250 |
| Tobacco hornworm (*Manduca sexta*) | 1-2 days | 10,000 |

EXAMPLE 5

A 2.0% agarose solution was prepared by dissolving 0.2 g of agarose in 10 ml of distilled water in a boiling water bath for approximately 5 minutes. The solution was cooled to 60° C. and maintained at this temperature in a constant temperature water bath to prevent premature gelation. A stock of fully swelled and expended water retentive polymer was prepared by soaking small crystals of water-swellable acrylic polymer in water for 1 day. The swollen crystal gels were then pushed through a wire screen to produce pieces that were approximately 1 mm in length, width, and height. Enough water swollen pieces were added to 1 ml aqueous dispersion containing approximately 10,000 nematodes (*Neoaplectana caprocapsae*) to increase the volume to 2 ml.

Two ml of agarose solution in a test tube previously maintained at 60° C. were taken out of the water bath and cooled to about 45° C. To this agarose solution, 2 ml of the above nematode-water retentive polymer dispersion were added with vortexing and the resulting mixture was poured immediately into a mold. Gelation occurred in about 5 to 10 seconds. The nematode macrogels in agarose were then covered with parafilm. The insect nematode agarose macrogels were stable for at least one year when stored below 16° C. Similar insect nematode macrogels have been prepared using carrageenan, agar, kappa-carrageenan, carbopol and guar gum, all with retention of activity.

EXAMPLE 6

A 2% gellan gum solution was prepared as described in Example 1. Enough water swollen pieces of water retentive polymers were added to a 1 ml aqueous suspension containing 4 mM calcium chloride and nuclear polyhedrosis viruses (NPV) isolated from diseased wax moth larvae to make a 2 ml solution (final concentration of calcium chloride was 2 mM). This NPV-water retentive polymer solution was then added with gentle vortexing to an equal volume of the 2% gellan gum solution at room temperature and quickly poured into plastic tubes. Gelation took approximately 10 minutes and the NPV macrogel tubes were then capped and stored at below 16° C. The NPV macrogels were stable for at least six months.

EXAMPLE 7

A 2% gellan gum solution was prepared as described in Example 1. Enough water swollen pieces of water retentive polymers were added to a 1 ml solution of crystal-spore complexes (2.5 mg/ml) from Bacillus thuringiensis subsp. kurstaki (Bt) containing 4 mM calcium chloride to make a 2 ml solution. To this solution was added, with gentle vortexing, 2 ml of the 2% gellan gum solution at room temperature and the resultant mixture was poured into plastic tubes. Macrogel tubes were then capped and stored below 16° C. The Bt crystal-spore macrogels were stable for at least six months.

Macrogels containing both Bt crystal-spore complexes and approximately 10,000 nematodes (Neoaplectana carpocapsae) were also prepared as described above by mixing these two entomopathogens together with gellan gum. Various macrogels were then cut into small cubes of 0.5 cm in length, width and height and placed on top of a diet for tobacco hornworms (*Manduca sexta*) in plastic containers measuring 3 cm in diameter and 10 cm in height. The combined insect nematode-Bt crystal macrogels were found to be more active against tobacco hornworms than either nematode macrogels or Bt crystal macrogels alone. Control macrogels without entomopathogens were inactive against tobacco hornworms.

EXAMPLE 8

A 2% gellan gum solution was prepared as described in Example 1. Enough water swollen pieces of water retentive polymers were added to a 1 ml aqueous suspension of fungal pathogen (*Beauveria bassiana*) spores containing small amounts of Tween-20 and 4 mM calcium chloride to make a 2 ml solution. The fungal pathogen-water retentive polymer dispersion was then added, with gentle vortexing, to 2 ml of gellan gum solution. The resultant mixture was poured into plastic tubes, capped, and stored below 16° C. These macrogels were stable for at least several months. Similar macrogels were also prepared from fungal pathogens *Metarrhizium anisopliae* and *Nomurea releyi*, all with retention of activity.

EXAMPLE 9

A 2% gellan gum and a 0.2 M calcium chloride solutions in deionized distilled water were prepared. To the 2% gellan gum solution was added with gentle vortexing an equal volume of the nematode-water retentive polymer dispersion as described in Example 2 except in the absence of calcium chloride. The resulting solution was sprayed on the surface of tobacco leaves. Calcium chloride solution (0.2 M) was then sprayed on top of the gellan gum-nematode-water retentive polymer to induce instant gelation. After about 2 hours, the leaves were fed to tobacco hornworms (*Manduca sexta*) and insects were dead 48 hours later. No mortality was found when control gels without nematodes were used. This example illustrates the usefulness of gelation by spraying with high concentration of a gelling agent (calcium chloride).

EXAMPLE 10

A 2% gellan gum solution was prepared as described in Example 1. Enough water swollen pieces of water retentive polymers were added to a 1 ml solution of crystal-spore complexes (2.5 mg/ml) from *Bacillus thuringiensis* subsp. kurstaki (Bt) containing 4 mM calcium chloride and 10% UV protectant Octyl-dimethyl PABA to make a 2 ml solution. To this solution was added, with vortexing, 2 ml of the 2% gellan gum solution. The resultant mixture was poured into plastic tubes, capped and stored below 16° C. The Bt crystal macrogels containing UV protectant were stable for at least six months. The hydrophobic nature of the UV protectant allows them to concentrate on top of the macrogels which offer advantage for protection against inactivation by sunlight. When the UV protectant-containing Bt macrogels were challenged with UV by irradiation with a GE germicidal lamp at a distance of 10 cm for 1 hour, full retention of biological activity against tobacco hornworms (*Manduca sexta*) was observed. Dimunition of activity was observed for unprotected macrogels.

EXAMPLE 11

Sweetgum sapwood measuring 2.5 by 3.8 by 0.6 cm were decayed with the Madison 617 isolate of *Gloeophyllum trabeum* (Persoon ex Fries) Murr. for 2 months or until about 15% of their weight was lost. The blocks were placed in sealed bags and irradiated with gamma-rays from a Cobalt-60 source for 6 hours (total dose 100 kRads). No live fungi were detected when the irradiated wood was spread on fresh 1.5% malt agar plate. A non-irradiated control showed extensive growth. Sawdusts were prepared from samples of (A) decayed, irradiated wood; (B) decayed, autoclaved(121° C., 15 minutes) wood; (C) decayed, non-irradiated wood; and (D) undecayed wood.

Fifteen termite workers (*Reticulitermes flavipes*) were released into an open air chamber containing pairs of the above described sawdusts located on opposite sides of the chamber. The number of termites attracted to each side was counted after five minutes.

| TEST | RELATIVE ATTRACTIVENESS |
|---|---|
| A vs. B | 13:2 |
| A vs. C | 15:0 |

| TEST | RELATIVE ATTRACTIVENESS |
|---|---|
| A vs. D | 15:0 |

EXAMPLE 12

The synergistic effect of combining raffinose with gamma-irradiated fungal-decayed wood prepared as in Example 11 was determined by observing the relative attractiveness of these materials to termites. Raffinose alone is a mild attractant for termites. Compared to raffinose, decayed wood is about twice as attractive and gamma-irradiated decayed wood three times as attractive. The combination of gamma-irradiated decayed wood and raffinose is about ten times as attractive as raffinose alone.

EXAMPLE 13

The utility of gamma-irradiated decayed wood was also demonstrated under field conditions by placing samples in a site free from termites and observing the surroundings for evidence of termite migration.

After two weeks of conditioning to the environment, samples were placed within 6 to 8 feet of a termite colony. Shortly thereafter, the termites migrated to the samples and completely destroyed them in 2 to 3 days. This test demonstrates the longevity of the attractant factor under field conditions and suggests utility of the gamma-irradiated fungal-decayed wood in a termite certification procedure.

EXAMPLE 14

A nematode-containing macrogel was prepared as in Example 2.

Samples of gamma-irradiated fungal-decayed wood sawdust prepared as in Example 11 were mixed with equal amounts of raffinose and coated onto the top of the nematode macrogel.

The gel was introduced into a Petri dish lined with damp filter paper and containing 20 termites (*Reticulitermes flavipes*). About ten pieces of wood from the termites' original colony were added as a competitive food source. Control dishes contained macrogel without nematodes.

After one day, 5 termites were dead. At two days, 9 termites had expired and by three days the total sample of 20 termites was exterminated. Ten termites were dissected at seven days and found to contain 5 to 10 nematodes per termite. All the control termites were still alive at six days when observation was ended.

When one of the infected, dead termites was introduced into a new dish containing 15 fresh, robust termites, all 15 expired within about 5 days due to spreading of the nematodes.

EXAMPLE 15

Three small nematode macrogels prepared as in Example 11 were introduced into a foraging chamber containing 600 termites and an ample abundance of wood. In two weeks 90% of the termites were dead. Dissection of dead termites revealed the presence of 5 to 10 live nematodes in each. No insect mortality was observed in a control chamber with blank macrogels.

What is claimed is:

1. An insecticidal macrogel comprising an insect-consumable continuous anionic gellan gum matrix containing at least one species of entomopathogen and a hydrated water retentive polymer which provides a reservoir of water for preventing dehydration of the entomopathogen, said polymer and said entomopathogen dispersed throughout said matrix, wherein said anionic gellan gum gels as a result of an addition of cations.

2. A macrogel of claim 1 in which said gum is gelled with divalent cations selected from the group consisting of barium, calcium, copper(II), iron(II), magnesium, manganese(II), and zinc(II) ions.

3. A macrogel of claim 1 in which said gum is gelled with monovalent cations selected from the group consisting of ammonium, cesium, lithium, potassium, and sodium ions.

4. A macrogel of claim 1 in which said gum is gelled with trivalent cations selected from the group consisting of Al(III) and Fe(III).

5. A macrogel of claim 1 in which the entomopathogens are selected from nematodes, bacteria, baculoviruses, and fungal pathogens.

6. A macrogel of claim 5 in which at least one entomopathogen is an insect nematode selected from the group consisting of *Neoaplectana carpocapsae* and *Heterorhabditis heliothidis*.

7. A macrogel of claim 5 in which the entomopathogen is nuclear polyhedrosis virus.

8. A macrogel of claim 5 in which the entomopathogen is a *Bacillus thuringiensis* or the crystal-spore complexes thereof.

9. A macrogel of claim 5 in which the entomopathogen is selected from the group consisting of *Beauveria bassiana*, *Metarrhizium anisopliae*, and *Nomurea releyi*.

10. A macrogel of claim 1 further comprising at least one agent capable of attracting insects to the macrogel, said agent included in, coated on, or in effective proximity to, said macrogel.

11. A macrogel of claim 10 in which said attractant agent is fungal-decayed wood or an attractive extract thereof.

12. A macrogel of claim 1 further comprising at least one agent for stimulating ingestion of the macrogel by the target insect.

13. A macrogel of claim 12 in which said agent is a saccharide selected from the group consisting of glucose, sucrose, mannose, and raffinose.

14. A macrogel of claim 1 further comprising at least one additional insecticide, biocide, fungicide or algicide.

15. A macrogel of claim 14 in the form of a cylinder, a cone, a sphere, a cube, or a rectilinear solid.

16. A macrogel of claim 14 having the shape of a funnel, tube or spike.

17. A macrogel of claim 1 further comprising a compound for imparting stability to ultraviolet radiation, said compound contained in, or on the surface of, said macrogel.

18. A macrogel of claim 1 in the form of a cylinder, a cone, a sphere, a cube, or a rectilinear solid.

19. A macrogel of claim 1 having the shape of a funnel, tube or spike.

20. A composition of claim 1 having from about 25% to about 75% by weight hydrated water retentive polymer and from a few to up to about 20% by weight entomopathogens, the remainder being matrix material and additives.

21. A macrogel of claim 1 wherein said species of entomopathogen are nematodes and *Bacillus thuringiensis*.

22. An insecticidal composition comprising at least one species of entomopathogen in an insect-consumable polysaccharide continuous matrix consisting essentially of glucuronic acid, rhamnose, glucose, and an O-glycosidically linked ester, said ester having up to about 5% O-acetyl groups, said composition having gamma-irradiated fungal-decayed wood or extract thereof as an attractant, said fungal-decayed wood exposed to irradiation effective to kill fungi without adversely affecting said attractant.

23. A composition of claim 22 in which the entomopathogen is a nematode.

24. A composition of claim 22 further comprising raffinose as an additional attractant.

25. A composition of claim 22 having up to about 20% by weight entomopathogens.

26. An insecticidal macrogel comprising an insect-consumable continuous matrix containing at least one species of entomopathogen, a hydrated water retentive polymer selected from the group consisting of a hydrophilic acrylic, acrylamide, vinyl and a polyurethane polymer, said water retentive polymer provides a reservoir of water for preventing dehydration of said entomopathogen, said polymer and said entomopathogen dispersed throughout said matrix.

27. An insecticidal macrogel comprising an insect-consumable continuous matrix containing at least one species of entomopathogen, a hydrated water retentive polymer which provides a reservoir of water for preventing dehydration of the entomopathogen, and at least one attractant selected from fungal decayed wood or extract thereof, said attractant exposed to irradiation effective to kill fungi without adversely affecting said attractant, said polymer and said entomopathogen dispersed throughout said matrix.

28. An insecticidal macrogel comprising an insect-consumable continuous matrix containing at least one species of entomopathogen, a hydrated water retentive polymer which provides a reservoir of water for preventing dehydration of the entomopathogen, and at least one attractant selected from fungi decayed wood or extract thereof, said attractant treated with gamma rays at a dose sufficient to kill fungi without adversely affecting said attractant, said polymer and said entomopathogen dispersed throughout said matrix.

* * * * *